(12) United States Patent
Elberg et al.

(10) Patent No.: US 6,440,169 B1
(45) Date of Patent: Aug. 27, 2002

(54) INTERSPINOUS STABILIZER TO BE FIXED TO SPINOUS PROCESSES OF TWO VERTEBRAE

(75) Inventors: Jean-François Elberg, Neuilly-sur-Seine; Erick Cloix, Bordeaux, both of (FR)

(73) Assignee: DIMSO (FR)

( * ) Notice: Subject to any disclaimer, the term of this patent is extended or adjusted under 35 U.S.C. 154(b) by 0 days.

(21) Appl. No.: 09/601,966

(22) PCT Filed: Jan. 27, 1999

(86) PCT No.: PCT/FR99/00154
§ 371 (c)(1),
(2), (4) Date: Oct. 17, 2000

(87) PCT Pub. No.: WO99/40866
PCT Pub. Date: Aug. 19, 1999

(30) Foreign Application Priority Data

Feb. 10, 1998 (FR) .............................................. 98 01528

(51) Int. Cl.⁷ .................................................. A61F 2/44
(52) U.S. Cl. .................................. 623/17.16; 623/17.11
(58) Field of Search ........................... 623/17.11, 17.12, 623/17.13, 17.14, 17.15, 17.16, 17.18; 606/61

(56) References Cited

U.S. PATENT DOCUMENTS 5,002,576 A * 3/1991 Fuhrmann et al. ............ 623/17
5,415,661 A   5/1995 Holmes ........................ 606/69
5,645,599 A * 7/1997 Samani ........................ 623/17
5,836,948 A * 11/1998 Zucherman et al. .......... 606/61
5,860,977 A   1/1999 Zucherman et al. .......... 606/61

FOREIGN PATENT DOCUMENTS

| DE | 31 13 142 A1 | * | 1/1982 |
| EP | 67 277 A2 | * | 10/1995 |
| EP | 0 820 731 A2 |  | 1/1998 |
| FR | 2 681 525 |  | 3/1993 |
| FR | 2 717 675 |  | 9/1995 |
| FR | 2 730 156 |  | 8/1996 |

* cited by examiner

Primary Examiner—Corrine McDermott
Assistant Examiner—Hieu Phan
(74) Attorney, Agent, or Firm—Lerner, David, Littenberg, Krumholz & Mentlik, LLP (57) ABSTRACT

The invention concerns an interspinous stabilizer comprising two members anchoring it to spinous processes of two respective vertebrae, and a body extending along a direction aligning the members, the body, being compressible along the alignment direction by the effect of stress based on a predetermined configuration, the body being adapted to recover spontaneously said predetermined configuration after the stress has ceased, the body comprising a leaf spring with a geometrical generatrix. The anchoring members are capable of fixing the stabilizer to the spinous processes such that the generatrix extends substantially from the front to the rear relative to the patient's body.

29 Claims, 6 Drawing Sheets

FIG_1

FIG_2

FIG_3

FIG_4

FIG_5

FIG_6

FIG_7

FIG_8

US 6,440,169 B1

INTERSPINOUS STABILIZER TO BE FIXED TO SPINOUS PROCESSES OF TWO VERTEBRAE

BACKGROUND OF THE INVENTION

1. Field of the Invention

The invention relates to interspinous stabilizers to be fixed to two vertebrae.

2. Description of Prior Art

A stabilizer of this type which includes two anchor members to be fixed to the vertebral pedicles of two vertebrae and a rigid body joining the two members together is known in the art. To treat degeneration of the disk, the stabilizer is used to immobilize the two vertebrae rigidly relative to each other and thereby to relieve the associated intervertebral disk. However, the stabilizer referred to is not entirely satisfactory. The surgery to fit the stabilizer requires access to the vertebral pedicles, or even the disk. It is therefore necessary to penetrate deeply into the body of the patient, which makes the operation more serious. What is more, because the two vertebrae are totally immobilized relative to each other, the disk is no longer loaded and continues to degenerate. Furthermore, the anchor members which are attached to the pedicles make them fragile and cause partial modification of the articular processes. Finally, fitting the anchor members requires delicate aiming in the pedicles so as not to exit from them and touch the dura mata, for example.

U.S. Pat. No. 5,645,599 discloses an interspinous stabilizer having members which are to be anchored to the spinous processes and which are joined together by a U-shaped leaf spring in a plane perpendicular to the geometrical generatrix of the spring. The stabilizer is adapted to be fixed to the spine so that the generatrix is parallel to the right-left direction referred to the body of the patient, the base of the U-shape being on the same side as the vertebral bodies and bearing against one of the vertebrae. Thus the stabilizer is entirely housed between the processes. It follows that the stabilizer is necessarily very small. This complicates its manufacture or makes it obligatory to give it a very simple shape to make it very rigid, which generates new risks of degeneration of the disk, as already mentioned.

SUMMARY OF THE INVENTION

An aim of the invention is to provide a different type of stabilizer and in particular one that is easy to manufacture an can be of low stiffness.

To achieve this object, the invention provides an interspinous stabilizer including two members adapted to be anchored to spinous processes of respective vertebrae and a body extending in a direction of alignment of the members, the body being compressible in the alignment direction and from a given configuration by the application of a force, the body being adapted to revert to the given configuration spontaneously after the force is removed, the body comprising a leaf spring having a geometrical generatrix, characterized in that the anchor members are adapted to fix the stabilizer to the processes so that the generatrix extends substantially from front to rear with reference to the body of the patient.

The stabilizer therefore allows some mobility of the two vertebrae relative to each other by partly reproducing the biomechanics of a healthy intervertebral disk. Moreover, the disk continues to be partly loaded, although the stabilizer relieves it of a great part of the stresses ordinarily imposed on it. Degeneration of the disk can therefore be slowed down or even stopped. The stabilizer preserves the integrity of the tripod articulation of the vertebral unit: the disk and the two posterior articulations and the associated connections at the level of a vertebra, namely the pedicles and the blades. Fitting the stabilizer to the spinous processes is a simple procedure. Also, the integrity of the protection of the dura mata is certain to be preserved.

What is more, orienting the generatrix in the front-rear direction enables the stabilizer to be extended laterally beyond the processes. Its volume can therefore be increased to make it both easier to manufacture and less rigid, if necessary, in order to limit the risk of degeneration of the disk.

The stabilizer according to the invention can also have one or more of the following features:
- the body comprises two leaf spring parts extending parallel to each other in the alignment direction;
- each part forms at least one U-shape in a plane perpendicular to the generatrix;
- the body comprises at least one leaf spring part forming at least two successive U-shapes in a plane perpendicular to the generatrix and oriented alternately in opposite directions;
- the spring has at least two sections of different thickness;
- the body includes two leaf springs bearing on each other;
- the leaf spring forms a closed loop;
- the loop is elliptical;
- the spring is thicker near a major axis of the ellipse than near a minor axis of the ellipse;
- the body includes at least one viscoelastic material member;
- the member is inside the loop;
- the body includes two viscoelastic material members near respective ends of a major axis of the ellipse; and
- the or each member has a cylindrical face in contact with a face of the spring.

The invention also provides an interspinous stabilizer including two members adapted to be anchored to spinous processes of respective vertebrae and a body extending in a direction of alignment of the members, the body being compressible in the alignment direction and from a given configuration by the application of a force, the body being adapted to revert to the given configuration spontaneously after the force is removed, in which the body has slots disposed to render the body compressible in the alignment direction.

The stabilizer according to the invention can also have one or more of the following features:
- the body is cylindrical and is hollowed out along an axis of the cylinder;
- the slots form at least one series of n adjacent slots symmetrically disposed about an axis of the cylinder and each slot subtends an angle greater than 180° about the axis;
- it includes at least two bodies which are parallel to each other in the alignment direction;
- at least one of the anchor members (2) comprises two toothed jaws (23) mobile axially towards each other to form a clamp.

BRIEF DESCRIPTION OF THE DRAWINGS

Other features and advantages of the invention will become more apparent in the course of the following description of preferred embodiments of the invention and variants thereof which are provided by way of non-limiting examples. In the accompanying drawings:

FIG. 1 is a view of a first preferred embodiment of a stabilizer according to the invention;

FIGS. 2 and 3 are respectively views of two variants of the first embodiment;

DESCRIPTION OF THE PREFERRED EMBODIMENTS

Figures 1, 2, 3:
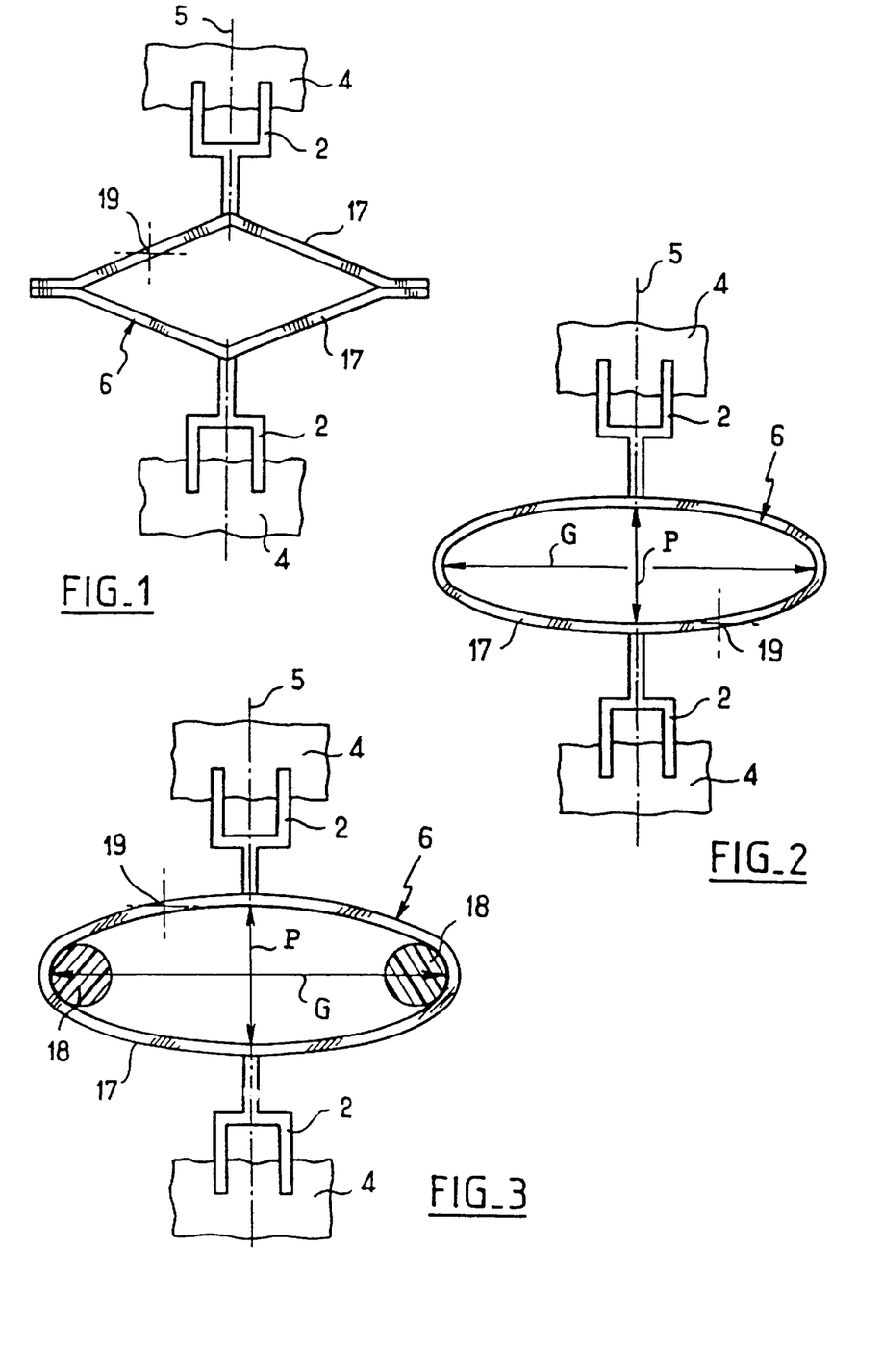

Referring to FIG. 1, in a first embodiment of the invention the stabilizer has two anchor members 2 of a type known in the art and adapted to be fixed rigidly to the spinous processes of respective adjacent vertebrae 4. The anchor members are of the type described in the document FR-2 722 980, for example. The stabilizer has a body 6 that extends between the anchor members 2 in a direction 5 of alignment of the anchor members and joins the anchor members together. The body 6 can be compressed in the direction 5 by a force tending to move the two processes towards each other. As shown in the figure, the body 6 has been compressed from a particular starting configuration. When the load is removed, the body 6 reverts spontaneously to its starting configuration. The two members 2 can also rotate relative to each other about a rotation point passing through the direction 5. By applying an appropriate force they can therefore be given a temporary relative inclination, the members 2 becoming parallel to each other again when the force is removed.

The body 6 includes two identical leaf springs 17 each of which has an elongate flat rectilinear shape. A middle portion of each spring 17 is fixed rigidly by one face to one end of one of the anchor members 2. The ends of the springs 17 are fixed together and bear on each other. The two springs 17 have a bend in their middle portion so that they form a lozenge. The leaf springs have a geometrical generatrix 19. The anchor members are positioned so that when the stabilizer has been fitted to the patient the generatrix 19 extends from front to rear with reference to the body of the patient and perpendicularly to the plane of FIG. 1. Only the edge of the spring 17 can be seen in FIG. 1. If a force is applied in the direction 5 to move the two anchor members 2 towards each other the lozenge is deformed substantially elastically and tends to flatten. When the force is removed the body 6 reverts to its original configuration by virtue of the stiffness of the spring 17. This embodiment allows the relative inclination of the anchor members 2 to be modified by application of an appropriate force, the inclination disappearing by virtue of their elasticity on removing the force that gave rise to it.

In the FIG. 2 variant, the body 6 has a single leaf spring 17 curved on itself to form an elliptical closed loop. The spring 17 is fixed rigidly to the anchor members 2 and lies between them so that the direction 5 constitutes the minor axis P of the ellipse. The generatrix 19 is oriented in the same manner as in the FIG. 1 embodiment. This stabilizer operates in essentially the same way as that shown in FIG. 1. The leaf spring 17 can advantageously have different thicknesses at different points. For example, the spring can have a greater thickness in the vicinity of the major axis G of the ellipse than in the vicinity of the minor axis P of the ellipse. Accordingly, the stiffness of the spring 17 depends on the part of the spring concerned. In particular this achieves non-uniform deformation of the various parts of the spring in response to application of a force in the direction 5.

In the FIG. 3 variant, the body 6 includes an elliptical spring 17 and two cores 18 made of a viscoelastic material such as polyurethane or silicone. Each core 18 is cylindrical. They are inside the ellipse, at the end of the major axis G, with their axes perpendicular to the axes P, G of the ellipse and parallel to the generatrix 19 of the spring. Their cylindrical face is in contact with the inside face of the spring. Each core 18 advantageously has a radius less than or equal to the smallest radius of curvature of the leaf spring at the level of the major axis G. The cores 18 modify the behavior of the body 6 when it is compressed and when it expands.

Figure 4:
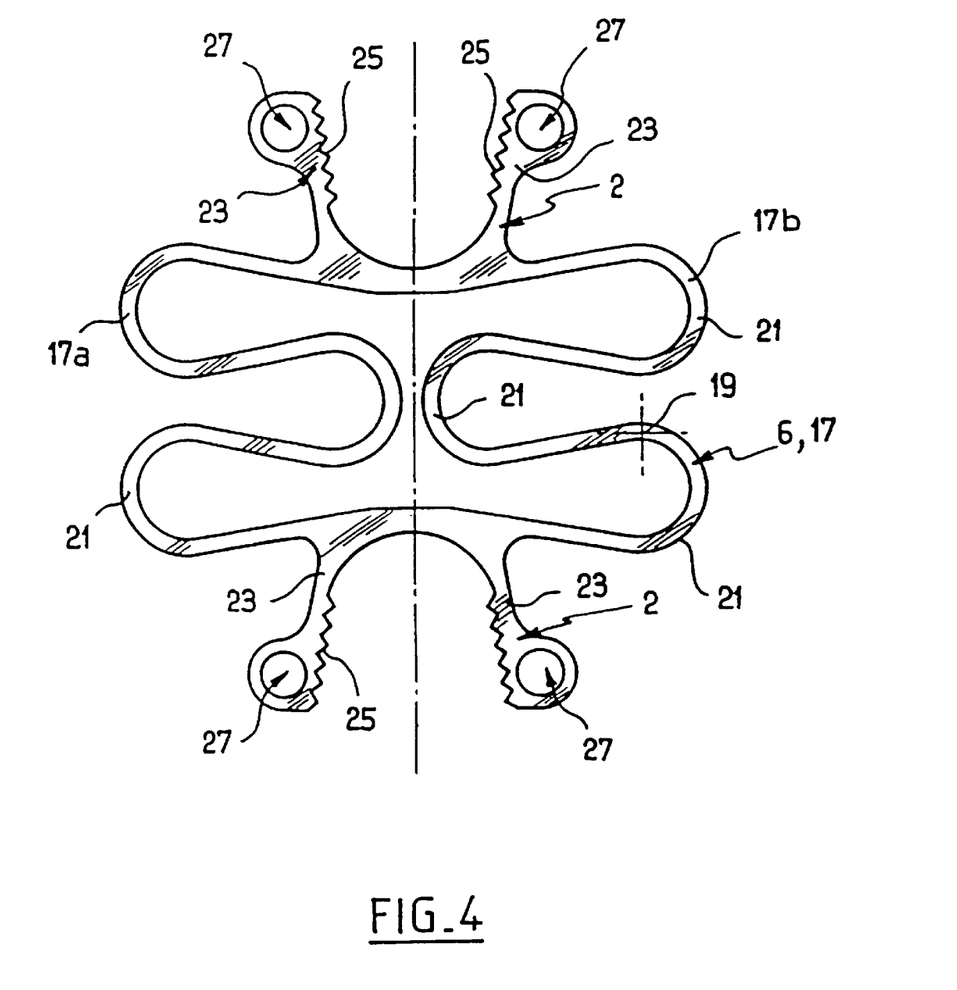
FIG. 4 is a view in elevation of a second preferred embodiment of a stabilizer according to the invention.
Figure 5:
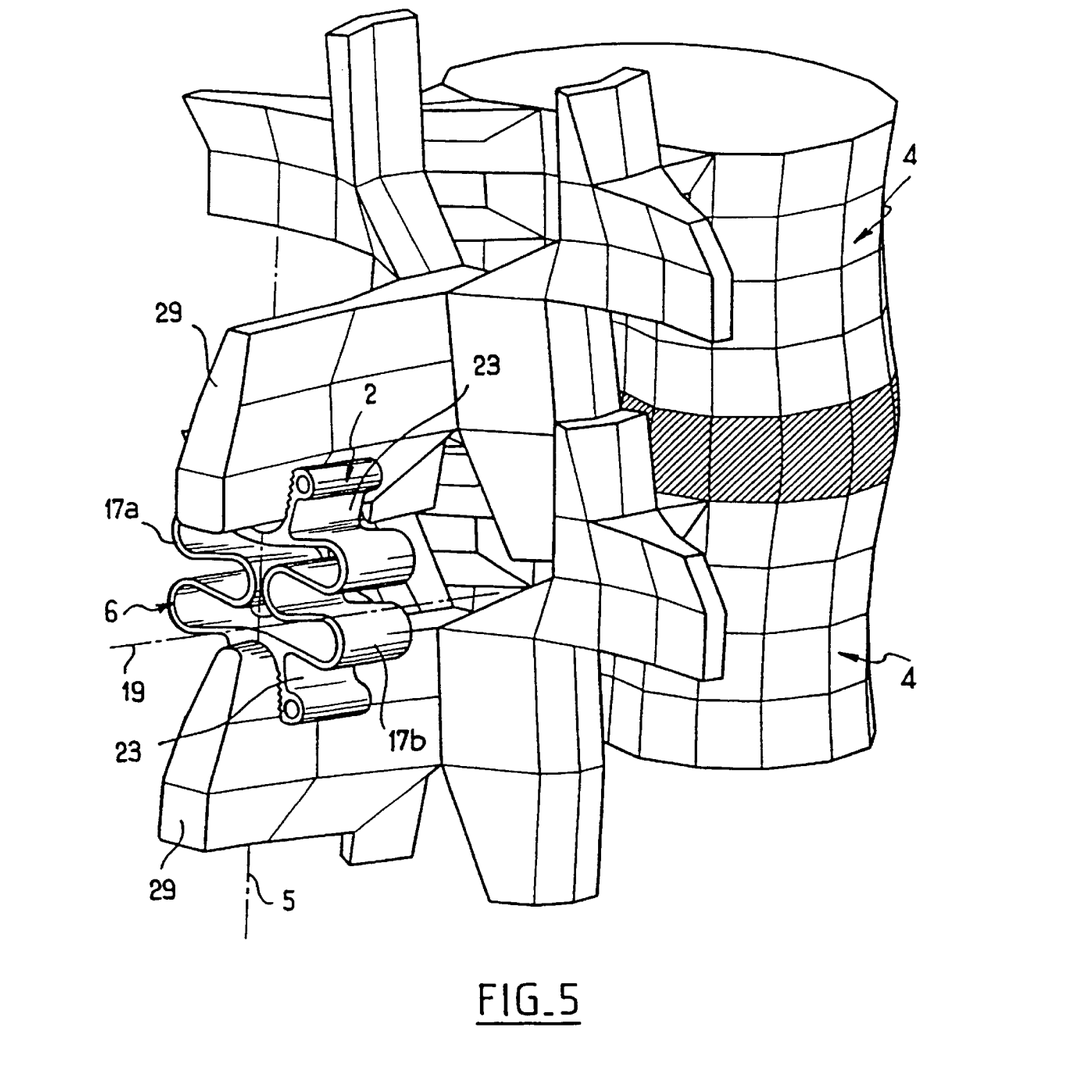
FIG. 5 is a perspective view of the stabilizer shown in FIG. 4 once it has been installed.

In the second embodiment, which is shown in FIGS. 4 and 5, the body 6 is again provided with a leaf spring 17 in the form of a closed loop and in one piece with the anchor members 2. The stabilizer is made of titanium or titanium alloy. As in the stabilizers shown in FIGS. 1, 2 and 3, the spring defines two leaf spring parts 17a, 17b extending parallel to each other in the alignment direction 5. The generatrix 19, which can also be seen in FIG. 5, again extends from front to rear.

The two parts 17a, 17b of the spring are symmetrical to each other with respect to a median plane passing through the axis 5. Each spring part forms a plurality of successive U-shapes alternately oriented in opposite directions in a plane perpendicular to the generatrix 19. Each part 17a, 17b has three of these U-shapes. The U-shapes nearest the anchor members 2 have their base 21 facing towards the outside of the stabilizer and the middle U-shape of each part has its base 21 facing towards the inside of the stabilizer. Each part 17a, 17b therefore forms an undulation or zig-zag. To be more precise, the general shape is that of an inverted M.

Each anchor member 2 comprises two jaws 23 which are symmetrical to each other with respect to the median plane, generally flat in shape and have a generatrix parallel to the generatrix 19. The two jaws 23 face each other. Their facing faces have profiled teeth 25. Each jaw has a passage 27 for inserting a tool for maneuvering the jaw and whose axis is parallel to the generatrix 19. The bases of the jaws extend at a distance from each other from one end of the spring 17. The two jaws are mobile elastically relative to each other. At rest they diverge from their base.

The whole of the stabilizer has the profile along an axis parallel to the generatrix 19 shown in FIG. 4.

To fit the stabilizer, the jaws 23 of each anchor member 2 are forced apart using tools inserted into the passages 27. The stabilizer is then placed as shown in FIG. 5 so that each process 29 is between the respective jaws 23. The jaws are then released so that they grip the processes and are anchored to them by their teeth 25.

As in the previous stabilizers, shown in FIGS. 1 to 3, the leaf spring parts 17a, 17b extend laterally beyond the processes 29, as shown in FIG. 5. They can be configured to impart a low stiffness to them. A stabilizer is fabricated by spark erosion from a mass of metal, this fabrication process being particularly simple because of the profile of the stabilizer. Like the stabilizers shown in FIGS. 1 to 3, this stabilizer has a relatively low stiffness for lateral flexing of the body, i.e. flexing about an axis parallel to the generatrix 19. It has a high stiffness for flexing of the body from front to rear, i.e. flexing about an axis perpendicular to the direction 5 and to the generatrix 19. The shape of the spring can easily be modified to increase or reduce at least one of the stiffnesses referred to above, independently of the volume available between the processes 29.

Figure 6:
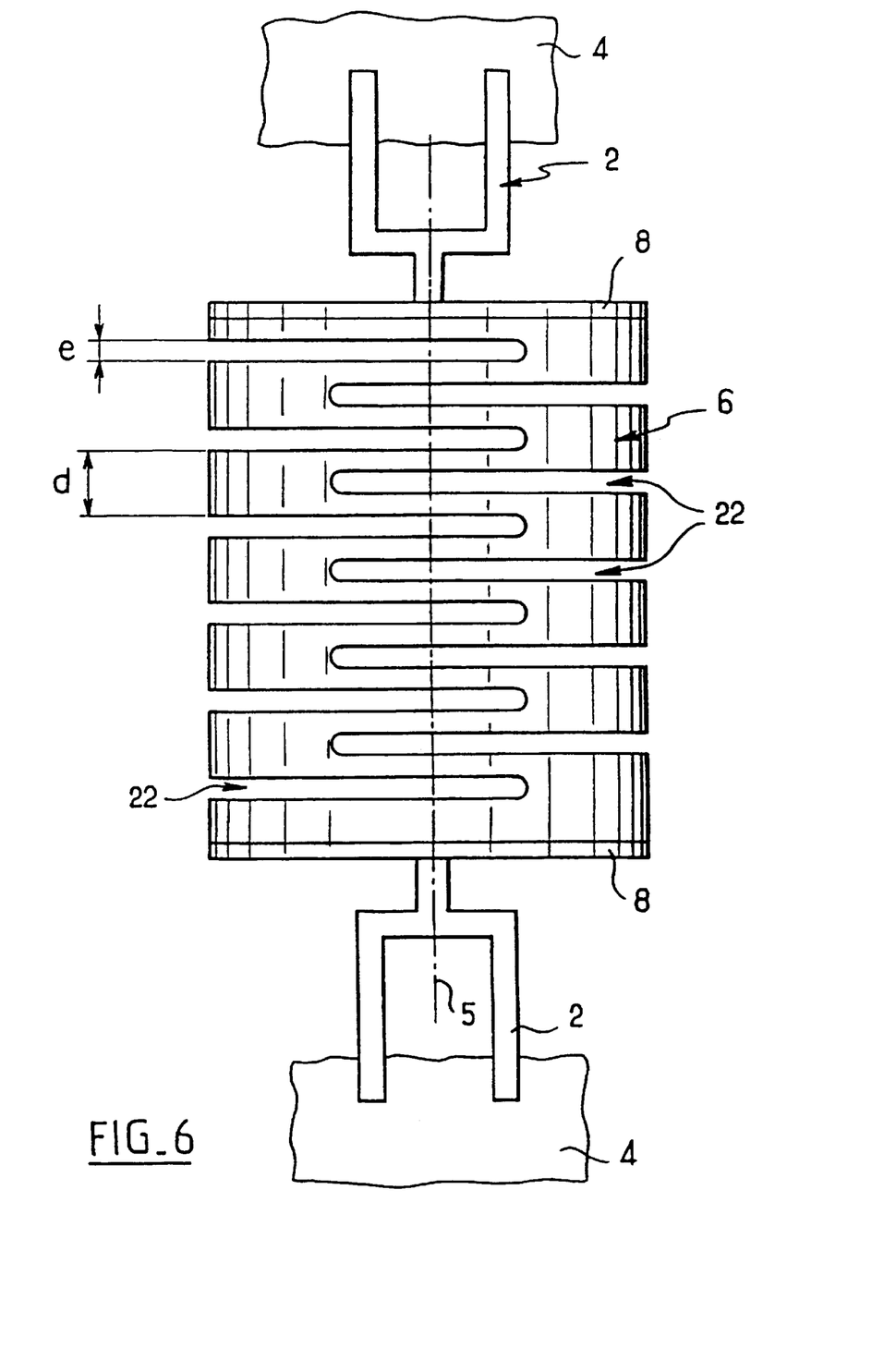
FIG. 6 is a front view of a third preferred embodiment of a stabilizer according to the invention.
Figure 7:
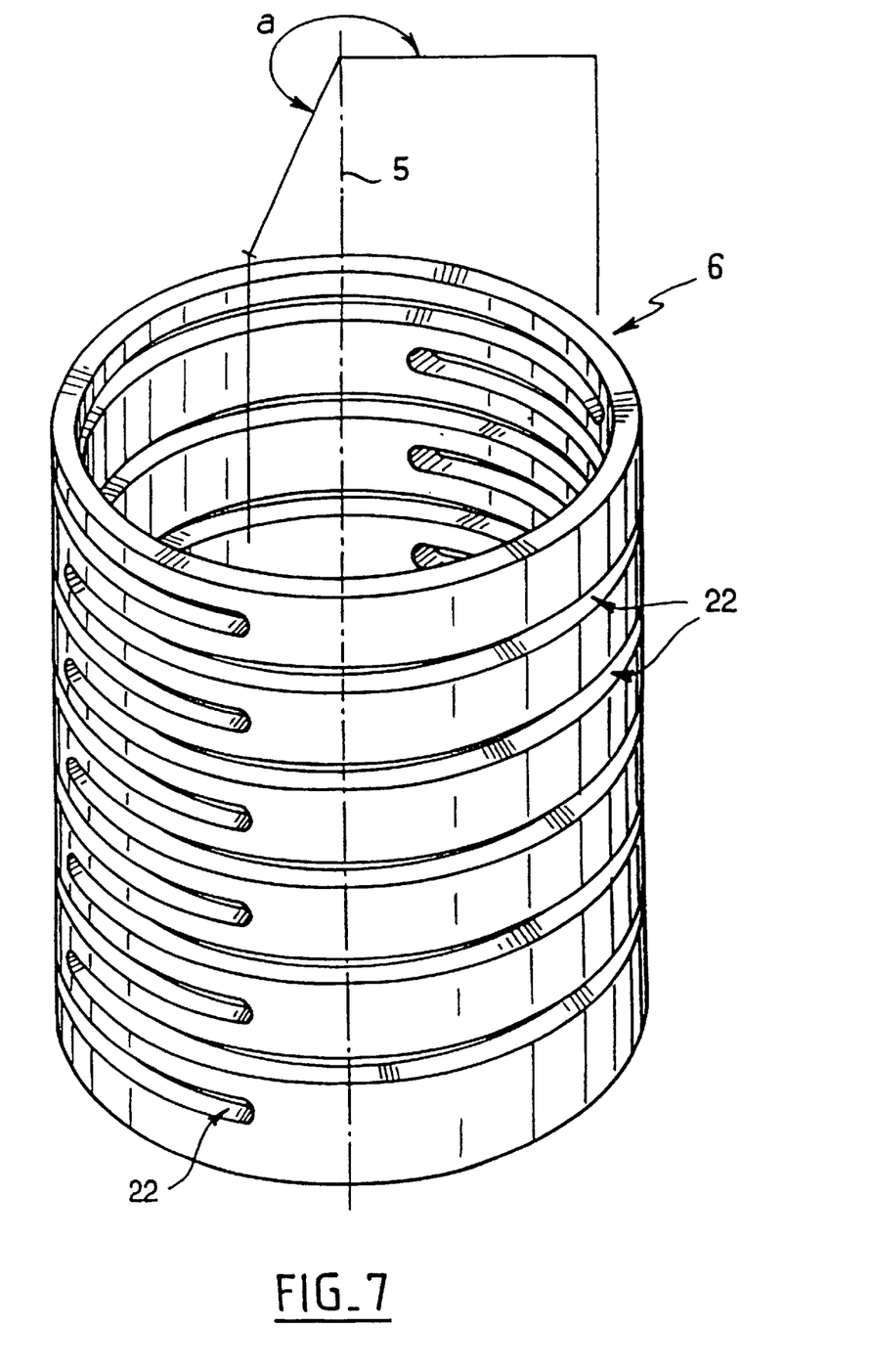
FIG. 7 is a perspective view of the body of the third embodiment.

Referring to FIGS. 6 and 7, in a third embodiment of the invention the stabilizer has two anchor members 2 to which respective plates 8 are fixed. The body 6 is cylindrical with a circular cross section and is hollowed out along an axis of the cylinder coincident with the alignment direction 5. The body 6 has two axial ends fixed rigidly to the respective plates 8. The body 6 has eleven slots 22 in its walls and each in a plane perpendicular to the direction 5. Each slot 22 subtends an angle greater than 180° about the axis 5. The slots 22 are divided symmetrically into two groups which are diametrally opposed and interleaved in the direction of the axis 5. The slots in each group coincide and are on the same side of the axis 5. The slots all have the same width e parallel to the axis 5. In both groups, the distance d between the adjacent slots of the same group is constant. This produces series each of which comprises two slots. The slots of each series are symmetrically disposed with respect to the axis 5.

This disposition of the slots imparts to the body 6 the function of a spring which is elastically compressible and expandable along the axis 5. The body is made from a suitable material such as a biocompatible metal. The body also allows the stabilizer to flex in any direction to allow the relative inclination of the two anchor members 2 previously referred to.

Figure 8:
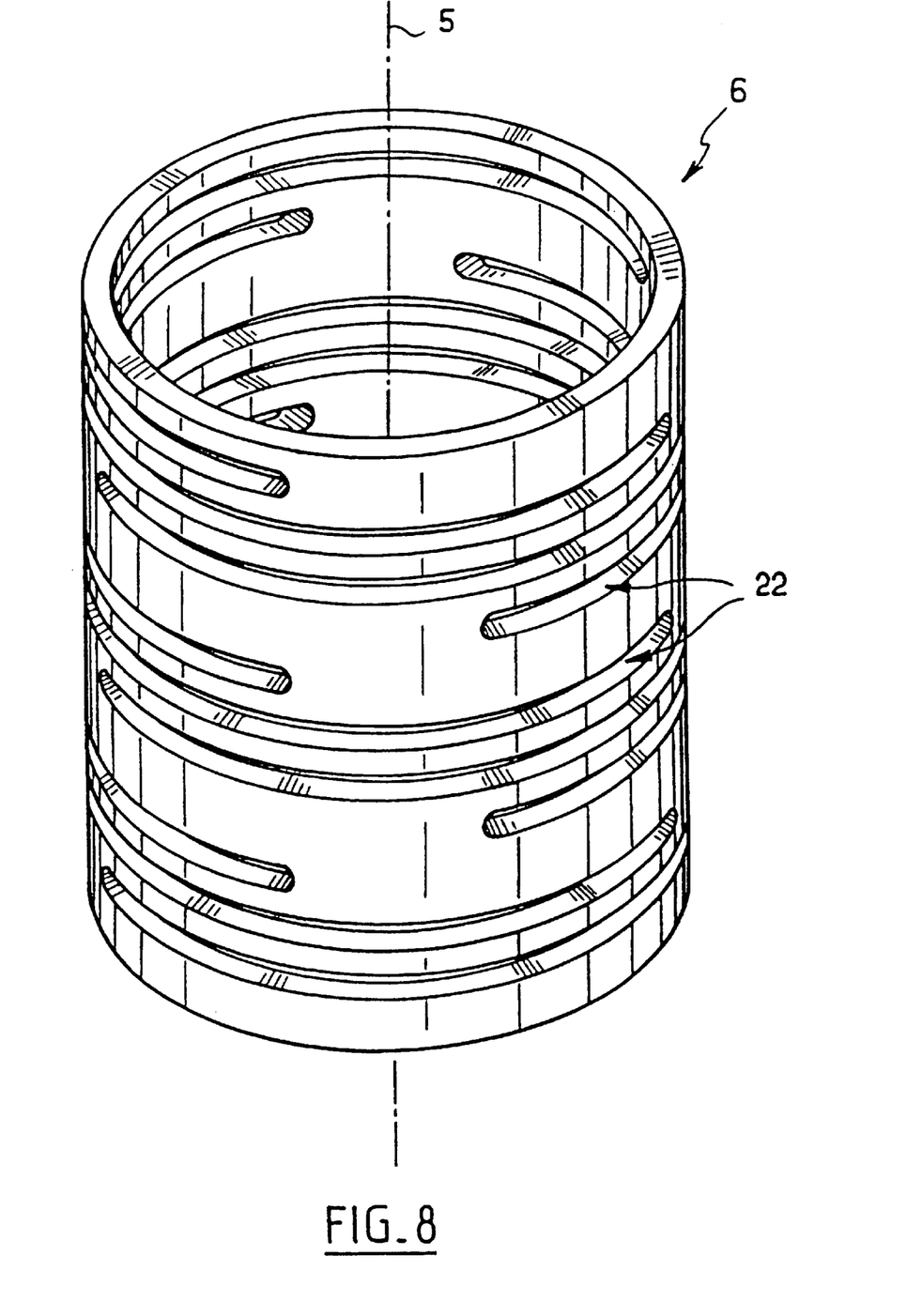
FIG. 8 is a view analogous to FIG. 7 showing a variant of the body.

In the FIG. 8 variant, the body 6 has slots 22 divided into four groups. The slots in each group coincide about the axis 5. Each slot subtends an angle greater than 180°. The slots of the four groups are regularly interleaved. This forms two series of four adjacent slots (at the top and in the middle in FIG. 1). The slots in each series are symmetrically disposed with respect to the axis 5.

In another variant the stabilizer could comprise a plurality of bodies 6 of the above type parallel to the direction 5.

The cylindrical body could have a non-circular cross section, for example an elliptical cross section.

The jaws 23 described with reference to the second embodiment can be incorporated into any other embodiment.

What is claimed is:

1. An interspinous stabilizer comprising two anchor members adapted to be anchored to spinous processes of respective vertebrae and having a body extending in a direction of alignment of the members, the body being resiliently compressible under forces acting in the alignment direction from a first configuration to a second configuration and reverting to the first configuration spontaneously after the force is removed, the body comprising a leaf spring having geometrically shaped walls defining an opening, the anchor members are adapted to fix the stabilizer to the processes so that walls of the leaf spring and the opening extend substantially in the anterior/posterior direction with reference to the body of the patient the walls closed in the medial-lateral direction.

2. The stabilizer according to claim 1, wherein the body comprises two leaf spring parts extending parallel to each other in the alignment direction.

3. The stabilizer according to claim 2, wherein the wall of each leaf spring, part has a U-shaped section.

4. The stabilizer according to any of claims 1 to 3, wherein the body comprises at least one leaf spring part forming at least two successive U-shapes in a plane perpendicular to the generatrix and oriented alternatively in opposite directions.

5. The stabilizer according to any of claims 1 to 3, wherein the leaf spring forms a closed loop.

6. The stabilizer according to claim 5, wherein the loop is elliptical.

7. The stabilizer according to any of claims 1 to 3, wherein the body includes at least one viscoelastic material member.

8. The stabilizer according to any of claims 1 to 3, wherein the body includes two leaf springs bearing on each other.

9. The stabilizer according to any of claims 1 to 3, wherein the leaf spring has at least two sections of different thickness.

10. The stabilizer according to claim 1, wherein at least one of the anchor members comprises two toothed jaws mobile axially towards each other to form a clamp.

11. The stabilizer according to claim 1, which includes at least two bodies which are parallel to each other in the alignment direction.

12. An interspinous stabilizer comprising two members for being anchored to spinous processes of respective vertebrae and a body extending in a direction of alignment of the members, the body being compressible in the alignment direction and from a given configuration by the application of a force, the body being adapted to revert to the given configuration spontaneously after the force is removed, the body having slots disposed to render the body compressible in the alignment direction, wherein the body is cylindrical and is hollowed out along an axis of the cylinder.

13. The stabilizer according to claim 12, wherein the slots form at least one series of at least two adjacent slots symmetrically disposed about an axis of the cylinder and each slot subtends an angle (a) greater than 180° about the axis.

14. The stabilizer according to claim 12, which includes at least two bodies which are parallel to each other in the alignment direction.

15. An interspinal vertebral implant comprising:
first and second anchor members, for fixing the implant to spinous processes of adjacent first and second vertebrae; and
a body having walls extending in an anterior/posterior direction, said walls forming a closed outer surface in the medial-lateral direction defining a shaped cavity therein, said cavity having two open ends, with a first end open in the anterior direction and a second end open in the posterior direction, said closed outer surface being resiliently deformable under pressure to compress said cavity.

16. The implant according to claim 15 wherein the body comprises two spring parts extending parallel to each other in the anterior-posterior direction.

17. The implant according to claim 16, wherein the closed outer surface has an oval cross-section.

18. The implant as set forth in claim 17, wherein the closed outer surface defines a cavity having at least two U-shaped portions extending in an anterior-posterior direction.

19. The implant as set forth in claim 15, wherein said cavity has at least one viscoelastic element therein.

20. The implant as set forth in claim 19, wherein said cavity has tightly curved portions which include said at least one viscoelastic member.

21. An interspinous stabilizer comprising two anchor members adapted to be anchored to spinous processes of respective vertebrae and having a body extending in a direction of alignment of the members, the body being resiliently compressible under forces acting in the alignment direction from a first configuration to a second configuration and reverting to the first configuration spontaneously after the force is removed, the body comprising a leaf spring having geometrically shaped walls defining an opening, the anchor members are adapted to fix the stabilizer to the processes so that walls of the leaf spring and the opening extend substantially in the anterior/posterior direction with reference to the body of the patient, wherein the body comprises two leaf spring parts extending parallel to each other in the alignment direction.

22. An interspinous stabilizer comprising two anchor members adapted to be anchored to spinous processes of respective vertebrae and having a body extending in a direction of alignment of the members, the body being resiliently compressible under forces acting in the alignment direction from a first configuration to a second configuration and reverting to the first configuration spontaneously after the force is removed, the body comprising two leaf springs having geometrically shaped walls defining an opening, the anchor members are adapted to fix the stabilizer to the processes so that walls of the leaf spring and the opening extend substantially in the anterior/posterior direction with reference to the body of the patient, wherein the two leaf springs bear on each other.

23. An interspinous stabilizer comprising two members for being anchored to spinous processes of respective vertebrae and a body having at least one portion extending in a direction of alignment of the members, the body being compressible in the alignment direction and from a given configuration by the application of a force, the body being adapted to revert to the given configuration spontaneously after the force is removed, the body portion having slots disposed to render the body compressible in the alignment direction wherein the body is cylindrical and is hollowed out along an axis of the cylinder which includes as least two body portions which are parallel to each other in the alignment direction.

24. An interspinal implant comprising:
first and second anchor members, for fixing the implant to spinous processes of adjacent first and second vertebrae; and
a body having walls extending in an anterior/posterior direction, said walls forming closed outer surface defining a shaped cavity therein, said cavity having two open ends, with a first end open in the anterior direction and a second end open in the posterior direction, said closed outer surface being resiliently deformable under pressure to compress said cavity wherein the body comprises two spring parts extending parallel to each other in the anterior-posterior direction.

25. The implant as set forth in claim 24, wherein the closed outer surface has an oval cross-section.

26. The implant as set forth in claim 25, wherein the closed outer surface defines a cavity having at least two U-shaped portions extending in an anterior-posterior direction.

27. An interspinal vertebral implant comprising:
first and second anchor members, for fixing the implant to spinous processes of adjacent first and second vertebrae;
a body having walls extending in an anterior/posterior direction, said walls forming closed outer surface defining a shaped cavity therein, said cavity having two open ends, with a first end open in the anterior direction and a second end open in the posterior direction, said closed outer surface being resiliently deformable under pressure to compress said cavity wherein the body comprises two spring parts extending parallel to each other in the anterior-posterior direction; and
said cavity has at least one viscoelastic element therein.

28. The implant as set forth in claim 27, wherein said cavity has tightly curved portion which include said at least one viscoelastic member.

29. An interspinous stabilizer comprising two anchor members adapted to be anchored to spinous processes of respective vertebrae and having a body extending in a direction of alignment of the members, the body being resiliently compressible under forces acting in the alignment direction from a first configuration to a second configuration and reverting to the first configuration spontaneously after the force is removed, the body comprising a leaf spring having geometrically shaped walls defining an opening, the anchor members are adapted to fix the stabilizer to the processes so that walls of the leaf spring and the opening extend substantially in the anterior/posterior direction with reference to the body of the patient, wherein the body comprises two leaf spring parts extending parallel to each other in the alignment direction which includes at least two bodies which are parallel to each other in the alignment direction.

* * * * *

UNITED STATES PATENT AND TRADEMARK OFFICE
CERTIFICATE OF CORRECTION

PATENT NO. : 6,440,169 B1  Page 1 of 1
DATED : August 27, 2002
INVENTOR(S) : Jean-Francois Elberg and Erick Cloix It is certified that error appears in the above-identified patent and that said Letters Patent is hereby corrected as shown below:

Column 1,
Line 47, "an" should read -- and --.

Column 5,
Line 63, after "patient" insert -- , --.
Line 63, after "walls" insert -- being --.

Column 6,
Line 2, cancel ",".

Column 7,
Line 40, "as" should read -- at --.

Column 8,
Line 29, "include" should read -- includes --.

Signed and Sealed this

Twenty-eighth Day of January, 2003

JAMES E. ROGAN
*Director of the United States Patent and Trademark Office*